United States Patent
Finlay et al.

(10) Patent No.: US 7,485,644 B2
(45) Date of Patent: Feb. 3, 2009

(54) N-{'4-SUBSTITUTED PIPERAZINE-1-SULFONYLMETHYLALKYL}-N-HYDROXYFOMAMIDE COMPOUNDS AS METALLOPROTEINASE INHIBITORS

(75) Inventors: Maurice Raymond Verschoyle Finlay, Macclesfield (GB); David Waterson, Macclesfield (GB)

(73) Assignee: AstraZeneca AB (SE)

( * ) Notice: Subject to any disclaimer, the term of this patent is extended or adjusted under 35 U.S.C. 154(b) by 277 days.

(21) Appl. No.: 10/561,747

(22) PCT Filed: Jun. 23, 2004

(86) PCT No.: PCT/GB2004/002702

§ 371 (c)(1),
(2), (4) Date: Dec. 21, 2005

(87) PCT Pub. No.: WO2005/000822

PCT Pub. Date: Jan. 6, 2005

(65) Prior Publication Data

US 2007/0197542 A1    Aug. 23, 2007

(30) Foreign Application Priority Data

Jun. 27, 2003    (SE) .................................. 0301922

(51) Int. Cl.
| | |
|---|---|
| A61K 31/497 | (2006.01) |
| A61K 31/4965 | (2006.01) |
| C07D 241/04 | (2006.01) |
| C07D 295/00 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |

(52) U.S. Cl. ............................ 514/252.14; 514/252.18; 514/253.11; 514/254.1; 514/255.03; 544/295; 544/360; 544/374; 544/383

(58) Field of Classification Search ............ 514/252.14, 514/252.18, 253.11, 254.1, 255.03; 544/295, 544/360, 374, 383
See application file for complete search history.

(56) References Cited

U.S. PATENT DOCUMENTS 6,734,184 B1 * 5/2004 Barlaam et al. ........ 514/252.12

FOREIGN PATENT DOCUMENTS

| WO | WO99/38843 | 8/1999 |
|---|---|---|
| WO | WO00/12478 | 3/2000 |
| WO | WO00/75108 | 12/2000 |
| WO | WO01/62742 | 8/2001 |
| WO | WO03/014092 | 2/2003 |

OTHER PUBLICATIONS

Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
West, Anthony R., Solid State Chemistry and Its Applications, Wiley, New York, 1988, 358.*

* cited by examiner

*Primary Examiner*—James O. Wilson
*Assistant Examiner*—Erich A Leeser
(74) *Attorney, Agent, or Firm*—Fish & Richardson P.C.

(57) ABSTRACT

The invention provides compounds of formula (I): or a pharmaceutically acceptable salt, prodrug or solvate thereof, wherein ring B represents a monocyclic aryl ring having six ring atoms or a monocyclic heteroaryl ring having up to six ring atoms and containing one or more ring heteroatoms wherein each said heteroatom is nitrogen; R2 represents a group selected from C1-6 alkyl or aryl, which said group is substituted by one or more fluorine groups; n is 1, 2 or 3; and R1 represents an optionally substituted group selected from C1-6 alkyl, C5-7 cycloalkyl, heterocycloalkyl, aryl, heteroaryl, C1-6 alkyl-aryl, C1-6 alkyl-heteroaryl, C1-6 alkyl-cycloalkyl or C1-6 alkyl-heterocycloalkyl. Processes for their preparation; pharmaceutical compositions containing them; and their use in the treatment of a disease condition mediated by one or more metalloproteinase enzymes.

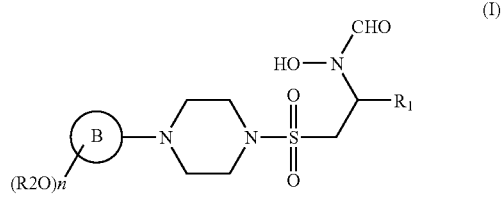

(I)

21 Claims, No Drawings

N-{'4-SUBSTITUTED PIPERAZINE-1-SULFONYLMETHYLALKYL}-N-HYDROXYFOMAMIDE COMPOUNDS AS METALLOPROTEINASE INHIBITORS

CROSS-REFERENCE TO RELATED APPLICATIONS

This application is a national phase application under 35 U.S.C. § 371 of PCT International Application No. PCT/GB2004/002702, filed Jun. 23, 2004, which claims priority to Swedish Application Serial No. 0301922-1, filed Jun. 27, 2003.

The present invention relates to certain N-hydroxyformamide derivatives useful in the inhibition of metalloproteinases, processes for their preparation, pharmaceutical compositions containing them, and their use in therapy.

The compounds of this invention are inhibitors of one or more metalloproteinase enzymes. Metalloproteinases are a superfamily of proteinases (enzymes) whose known numbers in recent years have increased dramatically. Based on structural and functional considerations these enzymes have been classified into families and subfamilies as described in N. M Hooper (1994) FEBS Letters 354:1-6. Examples of metalloproteinases include the matrix metalloproteinases (MMP) such as the collagenases (MMP1, MMP8, MMP13), the gelatinases (MMP2, MMP9), the stromelysins (MMP3, MMP10, MMP11), matrilysin (MMP7), metalloelastase (MMP12), enamelysin (MMP19), the MT-MMPs (MMP14, MMP15, MMP16, MMP17); the reprolysin or adamalysin or MDC family which includes the secretases and sheddases such as TNF converting enzymes (ADAM10 and TACE); the astacin family which include enzymes such as procollagen processing proteinase (PCP); and other metalloproteinases such as aggrecanase, the endothelin converting enzyme family and the angiotensin converting enzyme family.

Metalloproteinases are believed to be important in a plethora of physiological disease processes that involve tissue remodelling such as embryonic development, bone formation and uterine remodelling during menstruation. This is based on the ability of the metalloproteinases to cleave a broad range of matrix substrates such as collagen, proteoglycan and fibronectin. Metalloproteinases are also believed to be important in the processing, or secretion, of biological important cell mediators, such as tumour necrosis factor (TNF); and the post translational proteolysis processing, or shedding, of biologically important membrane proteins, such as the low affinity IgE receptor CD23 (for a more complete list see N. M. Hooper et al., (1997) Biochem J. 321:265-279).

Metalloproteinases have been associated with many disease conditions. Inhibition of the activity of one or more metalloproteinases may well be of benefit in these disease conditions, for example: various inflammatory and allergic diseases such as, inflammation of the joint (especially rheumatoid arthritis, osteoarthritis and gout), inflammation of the gastro-intestinal tract (especially inflammatory bowel disease, ulcerative colitis and gastritis), inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease)); in diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); Alzheimer's disease; extracellular matrix remodelling observed in cardiovascular diseases such as restenosis and atherosclerosis, and chronic obstructive pulmonary diseases, COPD (where MMP12 has been implicated).

A number of metalloproteinase inhibitors are known; different classes of compounds may have different degrees of potency and selectivity for inhibiting various metalloproteinases. The present inventors have discovered a new class of compounds that are inhibitors of metalloproteinases and are of particular interest in inhibiting collagenase 3 (also known as MMP-13). The compounds of this invention have beneficial potency and/or pharmacokinetic properties.

Collagenase 3 (MMP13) was initially cloned from a cDNA library derived from a breast tumour [J. M. P. Freije et al. (1994) Journal of Biological Chemistry 269(24):16766-16773]. PCR-RNA analysis of RNAs from a wide range of tissues indicated that collagenase 3 (MMP13) expression was limited to breast carcinomas as it was not found in breast fibroadenomas, normal or resting mammary gland, placenta, liver, ovary, uterus, prostate or parotid gland or in breast cancer cell lines (T47-D, MCF-7 and ZR75-1). Subsequent to this observation collagenase 3 (MMP13) has been detected in transformed epidermal keratinocytes [N. Johansson et al., (1997) Cell Growth Differ. 8(2):243-250], squamous cell carcinomas [N. Johansson et al., (1997) Am. J. Pathol. 151(2): 499-508] and epidermal tumours [K. Airola et al., (1997) J. Invest. Dermatol. 109(2):225-231]. These results are suggestive that collagenase 3 (MMP13) is secreted by transformed epithelial cells and may be involved in the extracellular matrix degradation and cell-matrix interaction associated with metastasis especially as observed in invasive breast cancer lesions and in malignant epithelia growth in skin carcinogenesis.

Recent published data implies that collagenase 3 (MMP13) plays a role in the turnover of other connective tissues. For instance, consistent with collagenase 3 (MMP13) substrate specificity and preference for degrading type II collagen [P. G. Mitchell et al., (1996) J. Clin. Invest. 97(3):761-768; V. Knauper et al., (1996) The Biochemical Journal 271:1544-1550], collagenase 3 (MMP13) has been hypothesised to serve a role during primary ossification and skeletal remodelling [M. Stahle-Backdahl et al., (1997) Lab. Invest. 76(5): 717-728; N. Johansson et al., (1997) Dev. Dyn. 208(3):387-397], in destructive joint diseases such as rheumatoid and osteo-arthritis [D. Wernicke et al., (1996) J. Rheumatol. 23:590-595; P. G. Mitchell et al., (1996) J. Clin. Invest. 97(3): 761-768; O. Lindy et al., (1997) Arthritis Rheum 40(8):1391-1399]; and during the aseptic loosening of hip replacements [S. Imai et al., (1998) J. Bone Joint Surg. Br. 80(4):701-710]. Collagenase 3 (MMP13) has also been implicated in chronic adult periodontitis as it has been localised to the epithelium of chronically inflamed mucosa human gingival tissue [V. J. Uitto et al., (1998) Am. J. Pathol 152(6):1489-1499] and in remodelling of the collagenous matrix in chronic wounds [M. Vaalamo et al., (1997) J. Invest. Dermatol. 109(1):96-101].

Compounds which inhibit the action of metalloproteinases, in particular collagenase 3 (MMP 13) are described in WO 00/12478, WO 00/75108 and WO 01/62742. Included among these reported inhibitors are aryl/heteroaryl piperazine sulfonylmethyl substituted N-hydroxyformamide compounds in which the aryl ring is substituted by a number of possible substitutents, including inter alia alkoxy and aryloxy. There is no disclosure that the alkoxy or aryloxy substitutent in such compounds may itself further be substituted.

Substituted alkoxy or aryloxy aryl/heteroaryl piperazine sulfonylmethyl substituted N-hydroxyformamide compounds as inhibitors of matrix metalloproteinases are encompassed within the general disclosure of WO 99/38843. Among the numerous possible substitutents for the alkoxy group listed is halogen. No such alkoxy substituted compound is disclosed, however and indeed, the only N-hydroxyformamide compound specifically disclosed is N-{1S-[4-(4-Chlorophenyl)piperazine-1-sulfonylmethyl]-2-methylpropyl}-N-hydroxyformamide.

The present inventors have found that substituted aryl or heteroaryl piperazine sulfonylmethyl substituted N-hydroxy formamide compounds in which the substitutent is an alkoxy group which itself is substituted by one or more fluorine groups are particularly advantageous metalloproteinase inhibitors, especially of collagenase 3 (MMP13), and have desirable activity profiles.

The present invention provides in a first aspect a compound of formula (I)

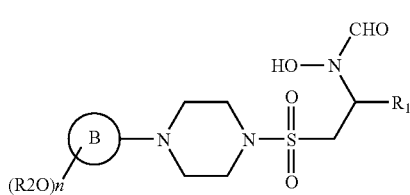

or a pharmaceutically acceptable salt, prodrug or solvate thereof, wherein ring B represents a monocyclic aryl ring having six ring atoms or a monocyclic heteroaryl ring having up to six ring atoms and containing one or more ring heteroatoms wherein each said heteroatom is nitrogen;

R2 represents a group selected from C1-6 alkyl or aryl, which said group is substituted by one or more fluorine groups;

n is 1, 2 or 3; and

R1 represents an optionally substituted group selected from C1-6 alkyl, C5-7 cycloalkyl, heterocycloalkyl, aryl, heteroaryl, C1-6 alkyl-aryl, C1-6alkyl-heteroaryl, C1-6 alkyl-cycloalkyl or C1-6alkyl-heterocycloalkyl.

As used herein, the term 'aryl' means an aromatic carbocyclic radical with one or two rings having up to ten ring atoms, such as phenyl or naphthyl. Where a single ring aromatic carbocyclic radical is intended, this is denoted a 'monocyclic aryl ring'. Where it is intended that an aryl ring has six ring atoms, this is specified.

'Heteroaryl' refers to aromatic ring systems having up to ten atoms, especially up to six ring atoms and comprising one or more ring heteroatoms, which may be the same or different, selected from N, O and S. Examples include pyrrolyl, furanyl, thiophenyl, imidazolyl, thiazolyl, pyridinyl, pyrimidinyl and pyrazinyl. Nitrogen heteroatoms will be substituted as necessary, and may also be in the form of N-oxides. Sulphur atoms may be in the form of S, S(O) or S(O$_2$). Where a single ring heteroaromatic system is intended, this is denoted a 'monocyclic heteroaryl ring' and where it is intended that a heteroaryl ring has a maximum number of ring atoms that is less than ten, this is specified. Where it is intended that a ring heteroatom is one of N, S or O in particular, or that the heteroaryl ring comprises more than one ring heteroatom, in specific combination, for example where each is the same, this is indicated.

The term "halogen" includes fluorine, chlorine, bromine and iodine, and in particular is fluorine.

Unless otherwise indicated, the term 'C1-6 alkyl', when used alone or in combination, refers to a straight or branched chain alkyl moiety having from one to six carbon atoms, including methyl, ethyl, propyl, isopropyl, butyl, tert-butyl, pentyl, hexyl and the like. 'C1-4 alkyl' will be understood accordingly to mean a straight or branched chain alkyl moiety having from one to four carbon atoms.

The term 'cycloalkyl' refers to a saturated alicyclic moiety having five, six or seven carbon atoms and includes, for example, cyclopentyl and cyclohexyl. A heterocycloalkyl ring refers to a saturated five, six or seven membered ring comprising one or more ring heteroatoms, which may be the same or different, selected from N, O and S and includes for example piperidinyl, pyrrolidinyl, tetrahydrofuranyl, tetrahydropyranyl.

'Optionally substituted' is used herein to indicate optional substitution by the group or groups specified at any suitable available position.

Suitably, ring B is a monocyclic aryl ring having six ring atoms such as phenyl or a monocyclic heteroaryl ring having up to six ring atoms and containing from one to four nitrogen ring atoms, such as pyridinyl or pyrimidinyl, triazinyl or tetrazinyl.

Where ring B is a heteroaryl ring, this is preferably a six-membered ring containing from one to four nitrogen ring atoms, even more preferably a six-membered ring containing one or two nitrogen ring atoms, such as pyridinyl or pyrimidinyl.

In one preferred embodiment, ring B is a phenyl ring.

In another preferred embodiment, ring B is a six-membered heteroaryl ring containing one or two nitrogen ring atoms. One preferred value for ring B is pyridinyl, especially 2-pyridinyl. A particularly preferred value for ring B is pyrimidinyl, more especially 2-pyrimidinyl.

R2 may be an aryl group having up to ten ring atoms, especially a monocyclic aryl group having six ring atoms (such as phenyl), substituted by one or more fluorine groups, but is preferably a C1-6 alkyl, especially C1-4 alkyl, group (such as methyl and especially ethyl) substituted by one or more fluorine groups.

Preferably R2 is substituted by one to five fluorine groups, especially by three or four fluorine groups.

In one preferred embodiment, R2 is C1-6 alkyl, especially C1-4 alkyl, substituted by three or four fluorine groups.

One preferred value for R2 is CF2CHF2.

In another particularly preferred embodiment, R2 is CH2CF3.

Suitably, n is 1 or 2 and is preferably 1. Preferably, the substitutent R2O— on ring B is para to the ring junction.

R1 is suitably an optionally substituted group selected from C1-4 alkyl (such as methyl or ethyl), aryl having six ring atoms (such as phenyl), five to six membered heterocycloalkyl ring comprising one or two ring heteroatoms, which may be the same or different, selected from N, O and S (such as piperidinyl or tetrahydropyranyl) or C1-4 alkyl-heteroaryl wherein the heteroaryl has up to six ring atoms and comprises one or two ring heteroatoms selected from N, O and S (such as alkyl pyrimidinyl or alkyl pyridinyl).

Preferably, R1 is an optionally substituted five to six membered heterocycloalkyl ring comprising one or two ring heteroatoms, which may be the same or different, selected from N, O and S, or a C1-4alkyl-heteroaryl group having up to six ring atoms and comprising one or more heteroatoms, which may be the same or different, selected from N, O and S, optionally substituted on the heteroaryl ring.

In one preferred embodiment, R1 is unsubstituted.

In one preferred embodiment, R1 is a tetrahydropyranyl group, especially 4-tetrahydropyranyl.

In another preferred embodiment, R1 is a C2-3alkyl-pyrimidinyl group, optionally substituted on the pyrimidinyl ring.

One preferred value for R1 is 2-pyrimidinyl-CH2CH2-. Another particularly preferred value for R1 is 2-pyrimidinyl-CH2CH2CH2-.

Suitable optional substitutents for R1 include one or more groups independently selected from NO2, CF3, CN, halogen, C1-4alkyl, carboxy(C1-4)alkyl, cycloalkyl, —OR4, —SR4, C1-4alkyl substituted with —OR4, SR4 (and its oxidised analogues), NR4, N—Y—R4, or C1-4alkyl-Y—NR4 where R4 is hydrogen, C1-6 alkyl, aryl, heteroaryl or C1-6 alkylaryl, each independently optionally substituted by halogen, NO2, CN, CF3, C1-6 alkyl, —S—C1-6 alkyl, —SO—C1-6 alkyl, —SO2-C1-6 alkyl or C1-6 alkoxy; and Y is selected from —SO2- and —CO—.

Where R1 in the compounds of formula (I) is substituted, this is preferably by one or two substitutents, which may be the same or different, selected from C1-4 alkyl, halogen, CF3 and CN. A preferred substitutent is halogen, particularly fluorine. Preferably where R1 is substituted, it is monosubstituted. One preferred value for R1 in the compounds of formula (I) where R1 is substituted is 5-F-2-pyrimidinyl-CH2CH2-

It will be appreciated that the number and nature of the substitutents on rings formed by R1 and/or R2 in the compounds of the invention will be selected so as to avoid sterically undesirable combinations.

In one preferred group of compounds according to the invention, R2 is C1-6 alkyl, substituted by one to five fluorine groups; n is 1; ring B is phenyl, pyridinyl or pyrimidinyl and R1 is an optionally substituted five to six membered heterocycloalkyl ring comprising one or two ring heteroatoms, which may be the same or different, selected from N, O and S, or a C1-4alkyl-heteroaryl group having up to six ring atoms and comprising one or more heteroatoms, which may be the same or different, selected from N, O and S, optionally substituted on the heteroaryl ring.

Particularly preferred compounds according to the invention within this group are those in which R1 is unsubstituted or is substituted by halogen, especially fluorine.

Specific compounds include

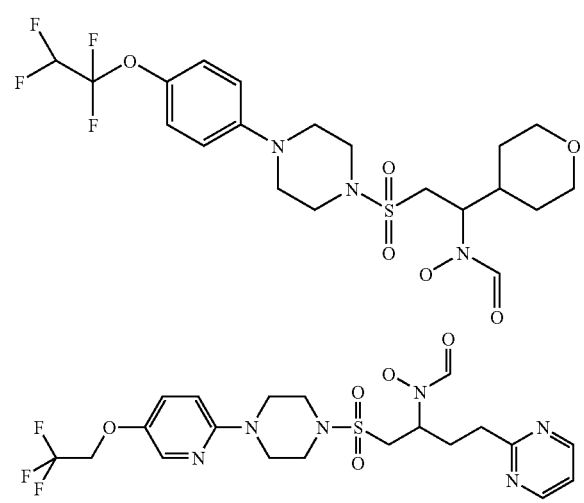

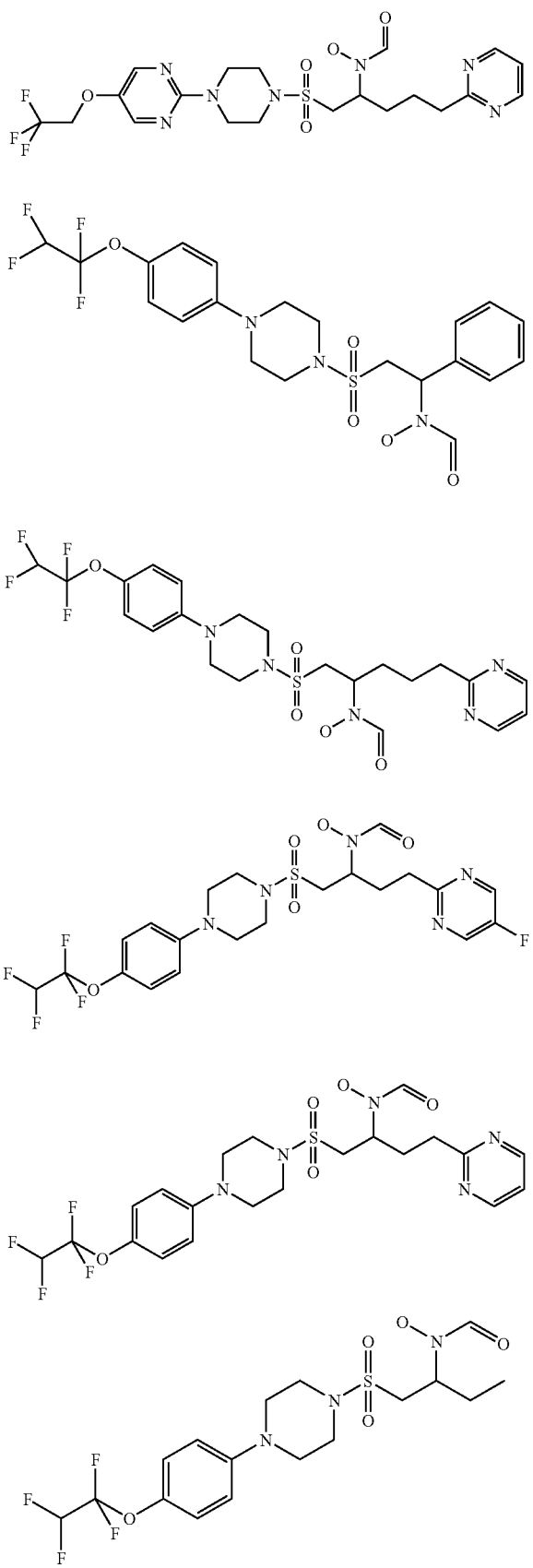

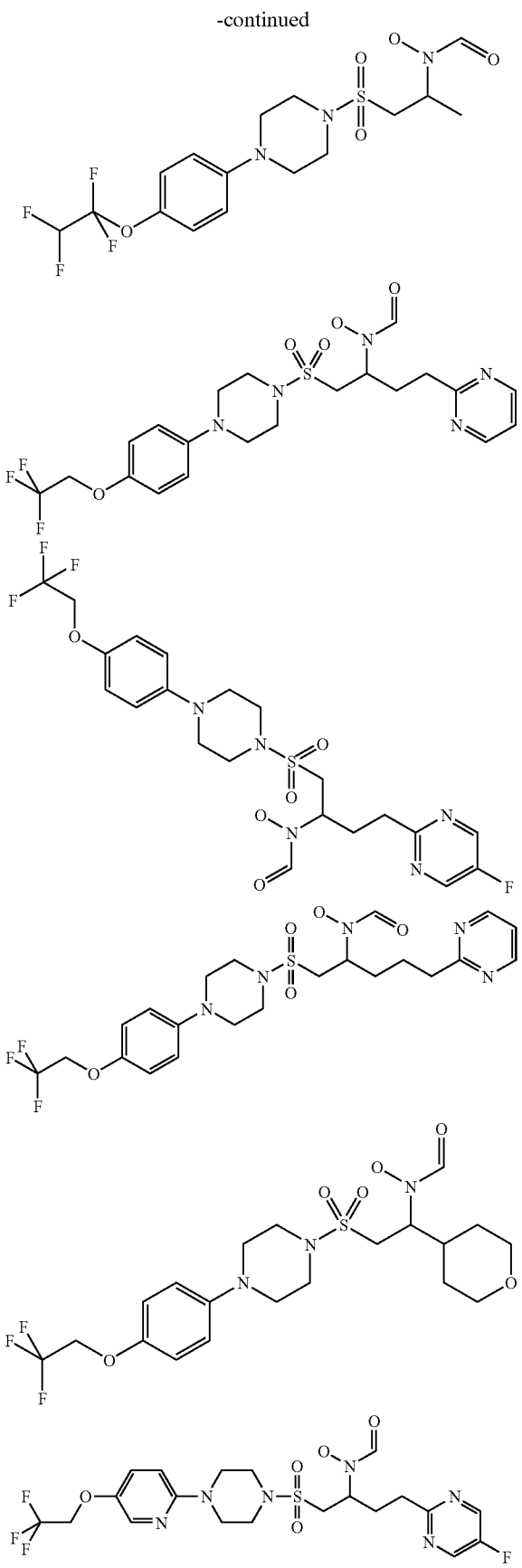

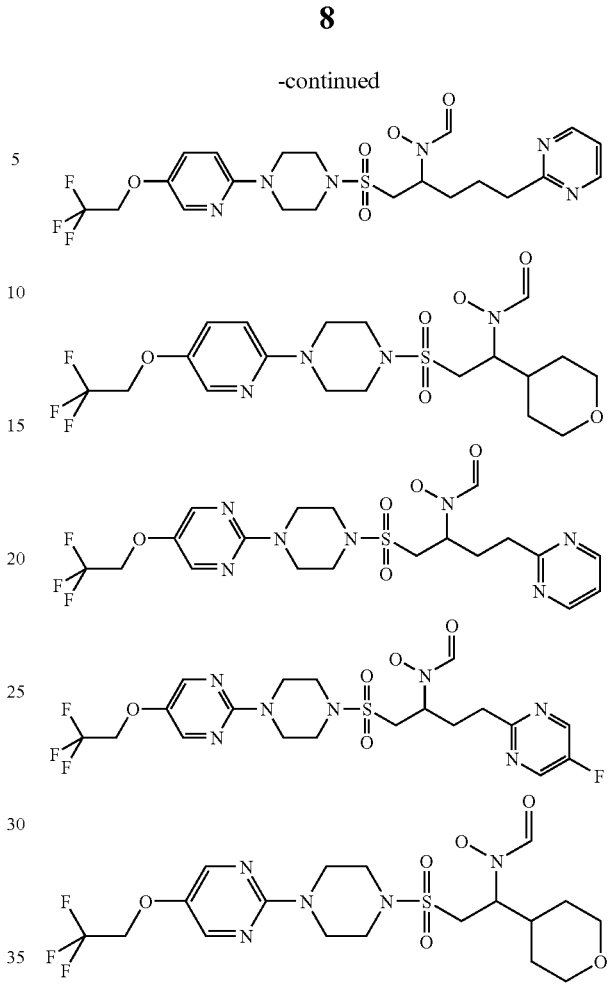

Where the compounds according to the invention contain one or more asymmetrically substituted carbon atoms, the invention includes all stereoisomers, including enantiomers and diastereomers, and mixtures including racemic mixtures thereof. Tautomers and mixtures thereof are also included.

Racemates may be separated into individual enantiomers using known procedures (cf. Advanced Organic Chemistry: 3rd Edition: author J March, p 104-107). A suitable procedure involves formation of diastereomeric derivatives by reaction of the racemic material with a chiral auxiliary, followed by separation, for example by chromatography, of the diastereomers and then cleavage of the auxiliary species.

Without wishing to be limited by initial determinations, it is believed that in the present case the active enantiomer has S stereochemistry. This is based on comparison with related compounds for which the absolute configuration has been confirmed. Accordingly, the S-structure is shown in the formulae given in the examples below. It will be appreciated, however, that a racemate of any compound according to the invention can be resolved into the individual enantiomers by the method outlined above and the more active enantiomer can then be identified by a suitable assay, without the need to determine absolute configurations.

The compounds according to the invention may be provided as pharmaceutically acceptable salts. Suitable pharmaceutically acceptable salts include base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. In another aspect, where the compound is sufficiently basic, suitable salts include acid addition salts such as methanesulphonate, fumarate, hydrochloride, hydrobromide, citrate, maleate and salts formed with phosphoric and sulphuric acid.

Suitable prodrugs of compounds of formula (I) are compounds which are hydrolysed in vivo to form compounds of formula (I). These may be prepared by conventional methods.

The present invention further provides a process for the preparation of a compound of formula (I) as defined above, or a pharmaceutically acceptable salt, prodrug or solvate thereof, which comprises:

converting the appropriate hydroxyamino compound of the formula (IV)

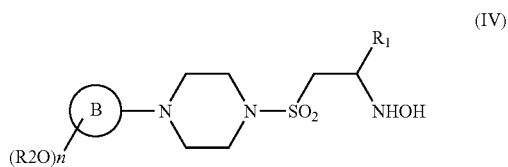

(IV)

(wherein R2, n, ring B and R1 are as defined in formula (I))
into a compound of formula (I) by formylation with an appropriate mixed anhydride; and thereafter, if necessary:

converting the compound obtained into a further compound according to the invention and/or forming a pharmaceutically acceptable salt or prodrug or solvate of the compound.

The formylation process may suitably be performed by reacting the compound of formula (IV) with the mixed anhydride prepared from reaction of formic acid and acetic anhydride. The reaction is conveniently performed in the presence of an organic acid such as formic acid. The reaction is preferably carried out in a suitable inert solvent or diluent, such as dichloromethane (DCM) or tetrahydrofuran and at a temperature in the range, for example, 0° C. to 50° C.

Compounds of formula (IV) may be prepared from the corresponding alkene of formula (III)

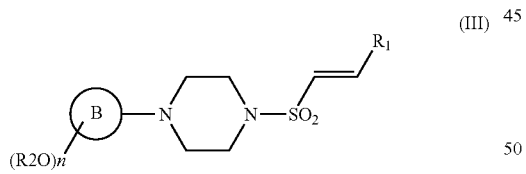

(III)

(wherein R2, n, B and R1 are as defined in formula (I)) which may itself be prepared from the corresponding compound of formula (II)

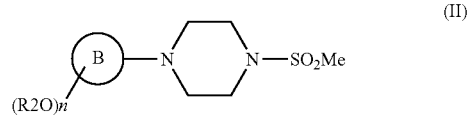

(II)

(wherein R2, n and ring B are as defined in formula (I)) by reaction with an appropriate compound of the formula R1CHO (wherein R1 is as defined for formula (I)) or by reaction with an appropriate ester to give a ketone, followed by reduction to the corresponding alcohol and dehydration. It will be appreciated that the compound of formula (III) may be in the form of the E- or Z-isomer, or as a mixture of both. The structure as shown in formula (I) is not intended to imply limitation to any particular geometrical isomerism around the double bond.

Compounds of formulae (III) and (IV) may be prepared using known techniques by methods analogous to those described in WO 00/12478, WO 00/75108 and WO 01/62742 above. Examples of preparation methods for certain of these compounds are given hereinafter in the examples.

Compounds of formula (II), (III) and (IV) are novel and form a further aspect of the invention. Specific compounds of formula (II) include:—

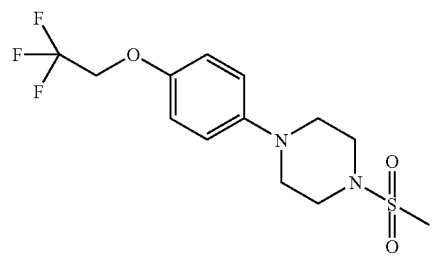

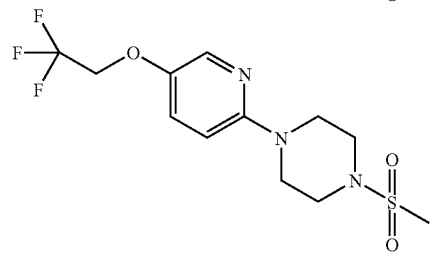

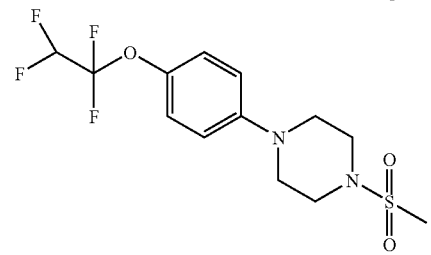

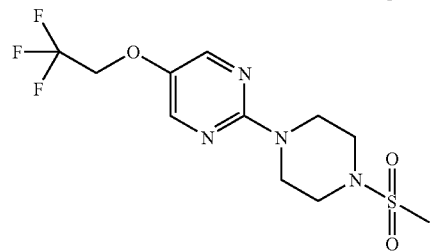

Examples of preparation methods for these compounds are given hereinafter in the examples.

Compounds of formula (I) can be converted into further compounds of formula (I) using standard procedures conventional in the art.

It will be appreciated that the preparation of compounds of formula (I) may involve, at various stages, the addition and removal of one or more protecting groups. The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of the invention are metalloproteinase inhibitors, in particular they are inhibitors of collagenase 3 (MMP13) and therefore are indicated in the treatment of diseases or conditions mediated by metalloproteinase enzymes including arthritis (such as osteoarthritis), atherosclerosis and chronic obstructive pulmonary diseases (COPD) as discussed above. In particular, the compounds of the invention are indicated in the treatment of diseases or conditions mediated by collagenase 3 (MMP13). A particular advantage of the collagenase 3 inhibitors according to the invention is that they exhibit improved selectivity over other metalloproteinases.

According to a further aspect, therefore, the present invention provides a compound of formula (I), or a pharmaceutically acceptable salt, prodrug or solvate thereof, as defined above for use in therapy of the human or animal body.

The invention also provides the use of a compound of formula (I), or a pharmaceutically acceptable salt, prodrug or solvate thereof, as defined above, in the manufacture of a to medicament for use in therapy.

It will be appreciated that "therapy" also includes "prophylaxis" unless otherwise indicated. The terms "therapeutic" and "therapeutically" will be understood accordingly.

In a yet further aspect the present invention provides a method of treating a metalloproteinase mediated disease condition which comprises administering to a warm-blooded animal a therapeutically effective amount of a compound of the formula (I) or a pharmaceutically acceptable salt, prodrug or solvate thereof.

It will be appreciated that dosage administered will vary depending on the compound employed, the mode of administration, the treatment desired and the disorder indicated. Typically, a daily dose of 0.5 to 75 mg/kg body weight (and preferably of 0.5 to 30 mg/kg body weight) is received. This daily dose may be given in divided doses as necessary, the precise amount of the compound received and the route of administration depending on the weight, age and sex of the patient being treated and on the particular disease condition being treated according to principles known in the art.

The compounds of formula (I) and pharmaceutically acceptable salts, prodrug and solvates thereof may be used on their own but will generally be administered in the form of a pharmaceutical composition in association with a pharmaceutically acceptable adjuvant, diluent or carrier.

The present invention therefore also provides a pharmaceutical composition comprising a compound of formula (I), or a pharmaceutically acceptable salt, prodrug or solvate thereof in association with a pharmaceutically acceptable adjuvant, diluent or carrier.

The pharmaceutical compositions of the invention may be administered in standard manner for the disease condition that it is desired to treat, for example by oral, topical, parenteral, buccal, nasal, vaginal or rectal administration or by inhalation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions.

In addition to the compounds of the present invention the pharmaceutical composition of the invention may also contain, or be co-administered (simultaneously or sequentially) with, one or more pharmacological agents of value in treating one or more disease conditions referred to above. Typically unit dosage forms will contain about 1 mg to 500 mg of a compound according to the invention.

The activity and selectivity of the compounds according to the invention may be determined using an appropriate enzyme inhibition test as described in WO 00/12478, WO 00/75108 and WO 01/62742. Collagenase 3 (MMP13) inhibitory activity may be assessed, for example, using the procedure set out below:—

Recombinant human proMMP13 may be expressed and purified as described by Knauper et al. [V. Knauper et al., (1996) The Biochemical Journal 271:1544-1550 (1996)]. The purified enzyme can be used to monitor inhibitors of activity as follows: purified proMMP13 is activated using 1 mM amino phenyl mercuric acid (APMA), 20 hours at 21° C.; the activated MMP13 (11.25 ng per assay) is incubated for 4-5 hours at 35° C. in assay buffer (0.1M Tris-HCl, pH 7.5 containing 0.1M NaCl, 20 mM CaCl2, 0.02 mM ZnCl and 0.05% (w/v) Brij 35 using the synthetic substrate 7-methoxycoumarin-4-yl)acetyl.Pro.Leu.Gly.Leu.N-3-(2,4-dinitrophenyl)-L-2,3-diaminopropionyl.Ala.Arg.NH$_2$ in the presence or absence of inhibitors. Activity is determined by measuring the fluorescence at λex 328 nm and λem 393 nm. By measuring the activity at a range of concentrations, a binding curve can be generated from which the IC50 can be determined, this figure being the inhibitor concentration at which the enzyme activity is reduced by 50%.

It will be appreciated that the pharmacological properties of the compounds of the invention will vary according to their structure but in general, compounds of the invention demonstrate collagenase 3 inhibitory activity as determined by the above assay at IC50 concentrations in the range 0.01 to 1000 nM. The following table shows IC50 figures for a representative selection of compounds according to the invention when tested in the above assay.

| Compound of Example No. | IC50 (nM) |
|---|---|
| 2b | 0.24 |
| 2f | 13.0 |
| 5 | 3.6 |
| 7a | 0.12 |
| 7c | 0.19 |
| 7f | 2.8 |
| 8b | 1.5 |
| 8g | 4.0 |

A compound of the Formula I may be used in combination with other drugs and therapies used in the treatment of disease states which would benefit from the inhibition of metalloproteinases, in particular collagenase 3 (MMP13). For example, a compound of the Formula I could be used in combination with drugs and therapies used in the treatment of rheumatoid arthritis, asthma, inflammatory bowel disease, multiple sclerosis, AIDS, septic shock, congestive heart failure, ischaemic heart disease, psoriasis and the other disease states mentioned earlier in this specification.

For example, by virtue of its ability to inhibit metalloproteinases, a compound of the Formula I is of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-administration of a compound of the Formula I of the present invention with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

A compound of the Formula I may also be used with anti-inflammatory agents such as an inhibitor of the enzyme 5-lipoxygenase.

A compound of the Formula I may also be used in the treatment of conditions such as rheumatoid arthritis in combination with antiarthritic agents such as gold, methotrexate, steroids and penicillinamine, and in conditions such as osteoarthritis in combination with steroids.

A compound of the Formula I may also be administered in degradative diseases, for example osteoarthritis, with chondroprotective, anti-degradative and/or reparative agents such as Diacerhein, hyaluronic acid formulations such as Hyalan, Rumalon, Arteparon and glucosamine salts such as Antril.

A compound of the Formula I may be used in the treatment of asthma in combination with antiasthmatic agents such as steroids, bronchodilators and leukotriene antagonists.

In particular, for the treatment of the inflammatory diseases rheumatoid arthritis, osteoarthritis, psoriasis, inflammatory bowel disease, chronic obstructive pulmonary disease, asthma and allergic rhinitis a compound of the present invention may be combined with agents such as TNF-α inhibitors such as anti-TNF monoclonal antibodies (such as Remicade, CDP-870 and $D_2E_7$.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold.

The present invention still further relates to the combination of a compound of the Formula I together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the Formula I together with a receptor antagonist for leukotrienes $LTB_4$, $LTC_4$, $LTD_4$, and $LTE_4$ selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the Formula I together with a PDE4 inhibitor including inhibitors of the isoform PDE4D.

The present invention still further relates to the combination of a compound of the Formula I together with a antihistaminic $H_1$. receptor antagonists such as cetirizine, loratadine, desloratadine, fexofenadine, astemizole, azelastine, and chlorpheniramine.

The present invention still further relates to the combination of a compound of the Formula I together with a gastroprotective $H_2$. receptor antagonist.

The present invention still further relates to the combination of a compound of the Formula I together with an $\alpha_1$.- and $\alpha_2$.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the Formula I together with anticholinergic agents such as ipratropium bromide; tiotropium bromide; oxitropium bromide; pirenzepine; and telenzepine.

The present invention still further relates to the combination of a compound of the Formula I together with a $\beta_1$.- to $\beta_4$.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the Formula I together with an insulin-like growth factor type I (IGF-1) mimetic.

The present invention still further relates to the combination of a compound of the Formula I together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the Formula I together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the C—$X_3$—C family.

The present invention still further relates to the combination of a compound of the Formula I together with antiviral agents such as Viracept, AZT, aciclovir and famciclovir, and antisepsis compounds such as Valant.

The present invention still further relates to the combination of a compound of the Formula I together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the Formula I together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the Formula I together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B.sub1.- and B.sub2.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK.sub1. and NK.sub3. receptor antagonists selected from the group consisting of NKP-608C; SB-233412 (talnetant); and D-4418; (xx) elastase inhibitors selected from the group consisting of UT-77 and ZD-0892; (xxi) TNF? converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

A compound of the Formula I may also be used in combination with osteoporosis agents such as roloxifene, droloxifene, lasofoxifene or fosomax and immunosuppressant agents such as FK-506, rapamycin, cyclosporine, azathioprine, and methotrexate.

A compound of the Formula I may also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

A compound of the Formula I can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD11839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multidrug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

If formulated as a fixed dose such combination products employ a compound of the Formula I within the dosage range described herein and the other pharmaceutically-active agent within its approved dosage range. Sequential use is contemplated when a combination formulation is inappropriate.

Although a compound of the Formula I is primarily of value as a therapeutic agent for use in warm-blooded animals (including man), it is also useful whenever it is required to inhibit the effects of a metalloproteinase. Thus, it is useful as pharmacological standard for use in the development of new biological tests and in the search for new pharmacological agents.

The invention is further illustrated by the following non-limiting examples.

The relevant starting materials are commercially available or may be made by any convenient method as described in the literature or known to the skilled chemist or described in the Examples herein. In addition the following table shows details of intermediates and their corresponding registry numbers in Chemical Abstracts.

|  | Chemical Abstracts Registry Numbers |
|---|---|
| 5-iodo-2-[4-(methylsulfonyl)piperazin-1-yl]pyrimidine | 497915-65-8 |
| ethyl 4-pyrimidin-2-ylbutanoate | 459818-75-8 |
| 4-pyrimidin-2ylbutanal | 260441-10-9 |
| ethyl 3-pyrimidin-2-ylpropanoate | 459818-76-9 |

In the Examples, nuclear magnetic resonance (NMR) spectra were measured at room temperature on a BRUKER DPX spectrometer operating at a field strength of 400 MHz, unless otherwise stated. The spectra were referenced to an internal deuterium lock. Mass spectroscopy (MS) spectra were measured on a Micromass MZD (electrospray) spectrometer.

The following abbreviations are used:—
DCM dichloromethane
THF tetrahydrofuran
LHMDS lithium hexamethyldisilazide
DMSO dimethylsulphoxide
TFA trifluoroacetic acid

EXAMPLE 1

Hydroxy{(1S)-4-pyrimidin-2-yl-1-[({4-[5-(2,2,2-trifluoroethoxy)pyrimidin-2-yl]piperazin-1-yl}sulfonyl)methyl]butyl}formamide

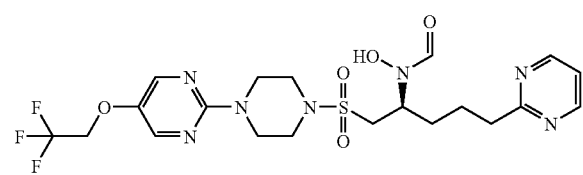

To formic acid (114 mL, 3.03 mol) at 0° C. was added acetic anhydride (28.6 mL, 0.303 mol) and the mixture was stirred at RT for 10 minutes. The reaction was then recooled to 0° C., and added to a solution of 2-(4-{[2-(hydroxyamino)-5-pyrimidin-2-ylpentyl]sulfonyl}piperazin-1-yl)-5-(2,2,2-trifluoroethoxy)pyrimidine (30.6 g, 60.5 mmol) and formic acid (114 mL, 3.03 mol) in THF (600 mL). The reaction was brought to room temperature and stirred for one hour. Volatiles were then removed in vacuo, and the residue azeotroped with toluene (2×300 mL). The residue was then dissolved in methanol (300 mL) and heated to 40° C. for one hour. The solution was then cooled to room temperature and concentrated in vacuo. The residue was then purified by flash chromatography (silica gel, 10% MeOH in EtOAc) to give the racemic compound as a pale orange foam (22.94 g, 43 mmol, 71%).

The racemic mixture was separated by chiral HPLC using conditions shown below:

| | |
|---|---|
| Column | 20 μm Chiralpak AD, Merck 100 mm |
| Eluent | MeCN/MeOH 90/10 (7 min, isocratic) MeCN/MeOH 90/10 (step) MeCN/MeOH 85/15 (10 min, isocratic) MeCN/MeOH 85/15 (gradient, 1 min) MeCN/EtOH 85/15 (isocratic, 37 min). |
| Flow | 120 ml/min |

The single enantiomers can be obtained in a crystalline form using the following procedure.

40 g of the title compound were stirred with ethanol (50 mL) at room temperature for 30 minutes. Solvent was remove in vacuo. The resulting solid was stirred in acetone (20 mL) at room temperature for 24 hours. Solvent was removed by a stream of Argon and then in vacuo.

$^1$H NMR (DMSO-D6, 373K): 9.39 (br s, 1 H), 8.67 (d, 2 H), 8.32 (s, 2H), 8.15 (br s, 1 H), 7.28 (t, 1 H), 4.70 (q, 2 H), 4.39 (br s, 1 H), 3.79 (m, 4 H), 3.47 (dd, 1 H), 3.29 (m, 4 H), 3.17 (dd, 1 H), 2.91 (m, 2 H), 1.75 (m, 4 H);

MS (ESI): 534.01 (MH+); Mpt 129-133° C.

The starting material was prepared as follows:

To a stirred suspension of 5-iodo-2-[4-(methylsulfonyl) piperazin-1-yl]pyrimidine (25.0 g, 67.9 mmol), benzyl alcohol (125 mL), 1,10-phenanthroline (2.45 g, 20 mol %), and cesium carbonate was added copper (I) iodide (12.9 g, 67.9 mmol) and the reaction heated to 110° C. for 90 minutes then cooled to room temperature. DCM (250 mL) was then added and the insolubles filtered off through a pad of celite. The cake washed with DCM (250 mL) and the DCM filtrates washed with water. The aqueous phase was then back extracted with more DCM (500 mL), the combined DCM extracts washed with brine (500 mL), dried (MgSO$_4$), filtered and concentrated in vacuo to a dark brown sludge. This was then purified by flash chromatography (silica gel, 50% EtOAc/hexanes) to give 5-(benzyloxy)-2-[4-(methylsulfonyl)piperazin-1-yl]pyrimidine as an off white solid (14.2 g, 40.7 mmol, 60%).

[1] H NMR (CDCl$_3$): 8.20 (s, 2 H), 7.49 (m, 5 H), 5.05 (s, 2 H), 3.88 (m, 4 H), 3.30 (m, 4 H), 2.79 (s, 3 H);

MS (ESI): 349.08 (MH+).

5-(benzyloxy)-2-[4-(methylsulfonyl)piperazin-1-yl]pyrimidine (57.9 g, 0.17 mol) was dissolved in TFA (600 mL) and the reaction heated to reflux, with stirring, for 7 hours then cooled to room temperature. The TFA was then in vacuo and the residue azeotroped with toluene (2×300 mL). The resulting solid was triturated with DCM, filtered off, washed with ether and dried to give 2-[4-(methylsulfonyl)piperazin-1-yl] pyrimidin-5-ol as a pale yellow solid (54.4 g, 0.15 mol, 88%, TFA salt).

[1] H NMR (DMSO-D6): 8.02 (s, 2 H), 3.68 (m, 4 H), 3.12 (m, 4 H), 2.86 (s, 3 H).

To a stirred suspension of 2-[4-(methylsulfonyl)piperazin-1-yl]pyrimidin-5-ol (53.5 g, 0.145 mol), K$_2$CO$_3$ (100.1 g, 0.725 mol) in acetone (1 L) was added 2,2,2-trifluoro ethyl nonafluorobutanesulphonate (78 g, 0.203 mol) and the reaction heated to 60° C. for 6 hours then cooled to room temperature. The reaction mixture was then filtered and the filtrate evaporated to dryness. The residue was partitioned between DCM (500 mL) and water (500 mL), extracted with DCM (500 mL), combined organics washed with brine (500 mL), dried (MgSO$_4$), filtered and concentrated in vacuo to give 2-[4-(methylsulfonyl)piperazin-1-yl]-5-(2,2,2-trifluoroethoxy)pyrimidine as an off white solid (45.3 g, 0.133 mol, 92%).

¹H NMR (CDCl₃): 8.15 (s, 2 H), 4.32 (m, 2 H), 3.90 (m, 4 H), 3.30 (m, 4 H), 2.78 (s, 3 H);

MS (ESI): 341.08 (MH⁺).

Method 1

To a stirred suspension of 2-[4-(methylsulfonyl)piperazin-1-yl]-5-(2,2,2-trifluoroethoxy)pyrimidine (8.05 g, 23.6 mmol) in THF (175 mL) at −78° C. was added LHMDS (47.2 mL, 47.2 mmol) dropwise and the reaction stirred for 15 minutes. A solution of ethyl 4-pyrimidin-2-ylbutanoate (5.5 g, 28.3 mmol) in THF (50 mL) was then added at −78° C., warmed to −20° C. and stirred for 2 hours. The reaction was then quenched by addition of a saturated solution of NH₄Cl (250 mL), extracted twice with EtOAc (2×250 mL), combined organics were washed with brine (250 mL), dried (MgSO₄), filtered and concentrated in vacuo to give a yellow solid. This was then purified by flash chromatography (silica gel, 50% EtOAc/hexanes) to give 5-pyrimidin-2-yl-1-({4-[5-(2,2,2-trifluoroethoxy)pyrimidin-2-yl]piperazin-1-yl}sulfonyl)pentan-2-one as an off white solid (9.47 g, 19.4 mmol, 82%).

¹H NMR (CDCl₃): 8.66 (d, 2 H), 8.16 (s, 2 H), 7.12 (t, 1 H), 4.30 (m, 2 H), 4.00 (s, 2 H), 3.82 (m, 4 H), 3.34 (m, 4 H), 2.98 (t, 2 H), 2.85 (t, 2 H), 2.16 (m, 2 H);

MS (ESI): 489.02 (MH⁺).

To a stirred solution of 5-pyrimidin-2-yl-1-({4-[5-(2,2,2-trifluoroethoxy)pyrimidin-2-yl]piperazin-1-yl}sulfonyl)pentan-2-one (9.47 g, 19.4 mmol) in DCM/MeOH (100 mL/100 mL) was added NaBH₄ (807 mg, 21.3 mmol) portionwise and the reaction stirred at room temperature. The reaction was then quenched by addition of a saturated solution of NH₄Cl (250 mL) and the organics removed in vacuo. The aqueous residue was then extracted with EtOAc (2×250 mL), combined organics washed with brine (250 mL), dried (MgSO₄), filtered and concentrated in vacuo to give 5-pyrimidin-2-yl-1-({4-[5-(2,2,2-trifluoroethoxy)pyrimidin-2-yl]piperazin-1-yl}sulfonyl)pentan-2-ol as a white solid (9.10 g, 18.6 mmol, 96%).

MS ESI): 491.13 (MH⁺).

To a stirred solution of the 5-pyrimidin-2-yl-1-({4-[5-(2,2,2-trifluoroethoxy)pyrimidin-2-yl]piperazin-1-yl}sulfonyl)pentan-2-ol (9.10 g, 18.6 mmol), triethylamine (13 mL, 93.0 mmol) in DCM (200 mL) at 0° C. was added methanesulfonyl chloride (2.16 mL, 27.9 mmol). The reaction was stirred at 0° C. for 15 minutes, warmed to room temperature and stirred for 16 hours. The reaction mixture was then washed with water (200 mL) and the aqueous back extracted with DCM (200 mL). The combined DCM extracts were washed with brine (250 mL), dried (MgSO₄), filtered and concentrated in vacuo to give 2-(4-{[(1E)-5-pyrimidin-2-ylpent-1-en-1-yl]sulfonyl}piperazin-1-yl)-5-(2,2,2-trifluoroethoxy)pyrimidine as an orange solid (8.79 g, 18.6 mmol, 100%).

MS (ESI): 472.49 (MH⁺).

To a stirred solution of 2-(4-{[(1E)-5-pyrimidin-2-ylpent-1-en-1-yl]sulfonyl}piperazin-1-yl)-5-(2,2,2-trifluoroethoxy)pyrimidine (8.79 g, 18.6 mmol) in THF (90 mL) was added 50% aqueous solution of hydroxylamine (18 mL) and the reaction stirred at room temperature for 2 hours. A saturated solution of NH₄Cl (200 mL) was then added and then this was extracted twice with extracted with EtOAc (2×250 mL), combined organics washed with brine (250 mL), dried (MgSO₄), filtered and concentrated in vacuo to give 2-(4-{[2-(hydroxyamino)-5-pyrimidin-2-ylpentyl]sulfonyl}piperazin-1-yl)-5-(2,2,2-trifluoroethoxy)pyrimidine as a pale yellow solid (8.96 g, 17.7 mmol, 95%).

MS (ESI): 506.05 (MH⁺).

Method 2

To a stirred suspension of 2-[4-(methylsulfonyl)piperazin-1-yl]-5-(2,2,2-trifluoroethoxy)pyrimidine (850 mg, 2.50 mmol) in THF (25 mL) at −78° C. was added LHMDS (5.5 mL, 5.5 mmol) dropwise and the reaction stirred for 15 minutes. Diethyl chlorophosphate (0.4 mL, 2.75 mmol) was then added and stirred for 15 minutes. The solution was then treated drop wise with a solution of 4-pyrimidin-2-ylbutanal (413 mg, 2.75 mmol) in THF (5 mL), allowed to warm to −20° C. and stirred for 1 hour. The reaction was then quenched by addition of a saturated solution of NH₄Cl (100 mL), extracted twice with EtOAc (2×100 mL), combined organics were washed with brine (100 mL), dried (MgSO₄), filtered and concentrated in vacuo to give a yellow oil. This was then purified by flash chromatography (silica gel, 50% EtOAc/hexanes) to give 2-(4-{[(1E)-5-pyrimidin-2-ylpent-1-en-1-yl]sulfonyl}piperazin-1-yl)-5-(2,2,2-trifluoroethoxy)pyrimidine as a yellow solid (1.13 g, 2.39 mmol, 96%).

MS (ESI): 472.49 (MH⁺).

This was then elaborated through to 2-(4-{[2-(hydroxyamino)-5-pyrimidin-2-ylpentyl]sulfonyl}piperazin-1-yl)-5-(2,2,2-trifluoroethoxy)pyrimidine and subsequently hydroxy{(1S)-4-pyrimidin-2-yl-1-[({4-[5-(2,2,2-trifluoroethoxy)pyrimidin-2-yl]piperazin-1-yl}sulfonyl)methyl]butyl}formamide via same procedure as in Method 1.

EXAMPLE 2

The following compounds were also prepared.

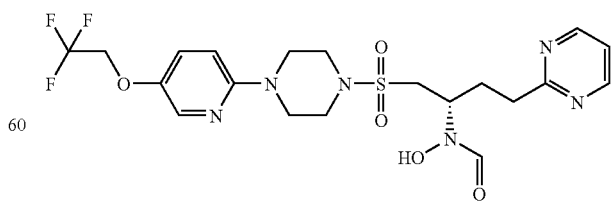

| No. | X | R1 | M + H | Prepared using method 1 or 2 |
|---|---|---|---|---|
| a | C | 2-PyrimidinylCH2CH2CH2 | 532.98 | 2 |
| b | C | 2-Pyrimidinyl-5-FluoroCH2CH2 | 537.10 | 2 |
| c | C | 4-Tetrahydropyranyl | 497.02 | 1 |
| d | N | 2-PyrimidinylCH2CH2 | 519.88 | 2 |
| e | N | 2-Pyrimidinyl-5-FluoroCH2CH2 | 537.89 | 2 |
| f | N | 4-Tetrahydropyranyl | 498.09 | 1 |

EXAMPLE 3

Hydroxy{(1S)-3-pyrimidin-2-yl-1-[({4-[5-(2,2,2-trifluoroethoxy)pyridin-2-yl]piperazin-1-yl}sulfonyl)methyl]propyl}formamide To formic acid (54 mL, 1.4 mol) at 8° C. was added acetic anhydride (11 mL, 100 mmol) and the mixture was stirred at RT for 10 minutes. The mixed anhydride was then recooled to 8° C., and added to a solution, pre-cooled to 0° C., 2-[3-(hydroxyamino)-4-({4-[5-(2,2,2-trifluoroethoxy)pyridin-2-yl]piperazin-1-yl}sulfonyl)butyl]pyrimidine (16.32 g, 33.3 mmol) in DCM (170 mL) and formic acid (65 mL, 1.7 mol). The reaction was brought to room temperature and stirred for one hour. Volatiles were then removed in vacuo, and the residue azeotroped with toluene (2×50 mL). The residue was then dissolved in MeOH/DCM (1:1, 250 mL) and stirred overnight at room temperature. The solution was then concentrated in vacuo, and partitioned between DCM (250 mL) and sat. NaHCO$_3$ (250 mL). The DCM layer was then filtered through silica gel (20 g) washing with 5% MeOH/DCM and the volatiles removed in vacuo to give the racemic title compound as a pale yellow foam (15.68 g, 302 mmol, 91%).

The racemic mixture (86.5 g) was separated into enantiomers by chiral HPLC using the following conditions:

| | |
|---|---|
| Column | 20 μm Chiralpak AD, Merck 100 mm |
| Eluent | MeCN/MeOH 90/10 (17 min, isocratic) MeCN/MeOH 90/10 (step) MeCN/EtOH 90/10 (8 min, isocratic) MeCN/EtOH 90/10 (gradient, 1 min) MeCN/EtOH 85/15 (isocratic, 39 min). |
| Flow | 120 ml/min |

Concentrated in vacuo to a foam. Crystallised from hot ethanol (430 mL), filtered and washed with ethanol and ether. Dried to give the title compound as a white crystalline solid (28 g, 54 mmol).

$^1$H NMR (DMSO, 373K): 9.41 (s, 1 H), 8.66 (d, 2 H), 8.07 (s, 1 H), 7.99 (d, 1H), 7.38 (dd, 1 H), 7.26 (t, 1 H), 6.83 (d, 1 H), 4.61 (q, 2 H), 4.45 (B, 1 H), 3.51 (t, 4 H), 3.47 (d, 1 H), 3.27 (t, 4 H), 3.24 (d, 1 H), 2.91 (t, 2 H), 2.17 (m, 2 H);

MS (ESI): 519 (MH$^+$);

Mpt 149-151° C.

The starting material was prepared as follows:

A vigorously stirred suspension of 1-(5-bromopyridin-2-yl)piperazine (CAS number 73406-97-0, 116 g, 479 mmol), 1,10-phenanthroline (17.3 g, 96 mmol), Cesium carbonate (312 g, 960 mmol) and Copper (I) iodide (91 g, 480 mmol) in benzyl alcohol (960 mL) was stirred at 120° C. under an inert atmosphere for 24 hours, adding further aliquots of copper (I) iodide (5×91 g) every hour. Cooled to 40° C. and diluted with DCM (1L), stirring at room temperature for 30 minutes. Filtered through celite, washing well with DCM (500 mL). The fractions were washed with NaOH (2M, 300 mL), combined and extracted with HCl (2M, 5×1L). The combined acidic extracts were washed with DCM (500 mL), cooled to 0° C. and extracted into DCM (1L), basifying slowly with NaOH (~46 wt %) to pH10. The aqueous layer was further extracted with DCM (2×500 mL) and the volatiles removed in vacuo, to give 1-[5-(benzyloxy)pyridin-2-yl]piperazine as a black liquor (104 g, 278 mmol @ 72 wt %, 58%).

$^1$H NMR (CDCl$_3$): 8.0 (d, 1 H), 7.2 (dd, 1 H), 6.3 (d, 1 H), 5.0 (s, 2 H), 3.50 (s, 8H), 1.48 (s, 9 H), 3.4 (13, 5 H), 3.0 (B, 4 H);

MS (ESI): 270 (MH$^+$).

A stirred solution of 1-[5-(benzyloxy)pyridin-2-yl]piperazine (104 g, 278 mmol) in CH$_2$Cl$_2$ (1.1L) at 0° C. was treated sequentially with triethylamine (94 mL, 672 mmol) and methanesulfonyl chloride (31 mL, 400 mmol). The reaction was brought to room temperature and stirred for 3 hour. The reaction was then diluted with DCM (3L) and washed with water (1L), HCl (0.5 M, 2×800 mL) and sat. NaHCO$_3$ (800 mL), back-extracting with DCM (500 mL). The combined organic extracts were then dried (MgSO$_4$), filtered and concentrated in vacuo to give 1-[5-(benzyloxy)pyridin-2-yl]-4-(methylsulfonyl)piperazine as a dark liquor (120 g, 278 mmol @ 81 wt %, 100%).

$^1$H NMR (CDCl$_3$): 8.0 (d, 1 H), 7.35 (m, 5 H), 7.2, (dd, 1 H), 6.65 (d, 1 H), 5.05 (s, 2 H), 3.55 (t, 4 H), 3.3 (t, 4 H), 2.8 (s, 3 H);

MS (ESI): 348 (MH$^+$).

1-[5-(benzyloxy)pyridin-2-yl]-4-(methylsulfonyl)piperazine (120 g, 278 mmol) was dissolved in TFA (1.3 L) and the reaction heated to reflux, with stirring, for 3 hours then cooled to room temperature. The TFA was then removed in vacuo and the residue azeotroped with toluene (2×300 mL). The resulting liquor was diluted with DCM (100 mL) and slowly neutralised to pH8 with sat. NaHCO$_3$ (700 mL). The suspension was filtered, washed with water, minimum DCM and ether and dried to give 6-[4-(methylsulfonyl)piperazin-1-yl]pyridin-3-ol as a beige solid (69 g, 270 mol, 97%).

$^1$H NMR (DMSO-D6): 7.7 (d, 1 H), 7.1 (dd, 1 H), 6.75 (d, 1 H), 3.45 (t, 4 H), 3.2 (t, 4 H), 2.85 (s, 3 H);

MS (ESI): 257 (MH$^+$).

To a stirred suspension of 6-[4-(methylsulfonyl)piperazin-1-yl]pyridin-3-ol (69 g, 270 mmol), K$_2$CO$_3$ (112 g, 810 mmol) in acetone (1.8 L) was added 2,2,2-trifluoroethyl nonafluorobutanesulphonate and/or 2,2,2-trifluoroethyl trifluoromethanesulphonate (total 324 mmol) and the reaction stirred for 18 hours at room temperature. The reaction mixture was then filtered and the filtrate evaporated to dryness. The residue was extracted between DCM (2.5 L, 500 mL) and water (1.5 L, 300 mL), extracted with DCM (500 mL), dried (MgSO$_4$) and filtered. Concentrated in vacuo, diluting with EtOH, to a low volume, filtered and dried to give 1-(methylsulfonyl)-4-[5-(2,2,2-trifluoroethoxy)pyridin-2-yl]piperazine as an off white solid (62 g, 183 mmol, 68%).

$^1$H NMR (CDCl$_3$): 8.0 (d, 1 H), 7.25 (dd, 1 H), 6.65 (d, 1 H), 4.3 (q, 2 H), 3.6 (t, 4 H), 3.35 (t, 4 H), 2.8 (s, 3 H);

MS (ESI): 340 (MH$^+$).

To a stirred suspension of 1-(methylsulfonyl)-4-[5-(2,2,2-trifluoroethoxy)pyridin-2-yl]piperazine (13.3 g, 39.2 mmol) in THF (200 mL) at −70° C. was added LHMDS (75 mL, 75 mmol) drop wise and the reaction stirred for 20 minutes. A solution of ethyl 3-pyrimidin-2-ylpropanoate (9.2 g, 51 mmol) in THF (55 mL) was then added at −70° C., warmed to −20° C. and stirred for 2 hours. The reaction was then quenched by addition of a saturated solution of NH$_4$Cl (250 mL), extracted twice with EtOAc (3×250 mL), combined organics were washed with brine (250 mL), dried (MgSO$_4$), filtered and concentrated in vacuo to give a yellow solid. The solid was stirred for 20 minutes in 20% isoHexane/ether (100 mL), filtered and washed with isoHexane and dried to give 4-pyrimidin-2-yl-1-({4-[5-(2,2,2-trifluoroethoxy)pyridin-2-yl]piperazin-1-yl}sulfonyl)butan-2-one as an off white solid (15.2 g, 32.2 mmol, 82%).

$^1$H NMR (CDCl$_3$): 8.6 (d, 2 H), 7.95 (d, 1 H), 7.2 (dd, 1 H), 7.1 (t, 1 H), 6.6 (d, 1 H), 4.30 (q, 2 H), 4.15 (s, 2 H), 3.55 (t, 4 H), 3.4 (t, 4 H), 3.35 (t, 2 H), 3.3 (t, 2 H);

MS (ESI): 472 (MH$^+$).

To a stirred solution of 4-pyrimidin-2-yl-1-({4-[5-(2,2,2-trifluoroethoxy)pyridin-2-yl]piperazin-1-yl}sulfonyl)butan-2-one (15 g, 31.6 mmol) in 10% MeOH/DCM (300 mL) was added NaBH$_4$ (0.52 g, 15.8 mmol) portionwise and the reaction stirred at room temperature for 45 minutes. The reaction was then quenched by addition of a saturated solution of NH₄Cl (100 mL), diluted with water (150 mL) and extracted with DCM (3×200 mL), combined organics dried (brine, MgSO₄), filtered and concentrated in vacuo. Triturated with ether, filtered and dried to give 4-pyrimidin-2-yl-1-({4-[5-(2,2,2-trifluoroethoxy)pyrimidin-2-yl]piperazin-1-yl}sulfonyl)butan-2-ol as a cream solid (13.8 g, 29.0 mmol, 92%).

MS (ESI): 476 (MH⁺).

To a stirred solution of the 4-pyrimidin-2-yl-1-({4-[5-(2,2,2-trifluoroethoxy)pyridin-2-yl]piperazin-1-yl}sulfonyl)butan-2-ol (13.7 g, 28.8 mmol) in DCM (250 mL) at 0° C. was added methanesulfonyl chloride (2.68 mL, 34.6 mmol). The reaction was stirred at 0° C. for 20 minutes before dropwise addition of triethylamine (18.1 mL, 129 mmol). Warmed to room temperature and stirred for 16 hours. The reaction mixture was then diluted with DCM (1 L), washed with water (150 mL) and dried (brine, MgSO₄), filtered and concentrated in vacuo. The residue was then purified by flash chromatography (silica, 0-5% MeOH in DCM) to give 2-[(3E)-4-({4-[5-(2,2,2-trifluoroethoxy)pyridin-2-yl]piperazin-1-yl}sulfonyl)but-3-en-1-yl]pyrimidine as a yellow solid (11.9 g, 18.6 mmol, 90%).

MS (ESI): 458 (MH⁺).

To a stirred solution of 2-[(3E)-4-({4-[5-(2,2,2-trifluoroethoxy)pyridin-2-yl]piperazin-1-yl}sulfonyl)but-3-en-1-yl]pyrimidine (10.9 g, 23.7 mmol) in THF (200 mL) was added 50% aqueous solution of hydroxylamine (11 mL) and the reaction stirred at room temperature for 2 hours. Water (100 mL) was then added and then this was extracted with EtOAc (3×100 mL) and dried (brine, MgSO₄), filtered and concentrated in vacuo to give 2-[3-(hydroxyamino)-4-({4-[5-(2,2,2-trifluoroethoxy)pyridin-2-yl]piperazin-1-yl}sulfonyl)butyl]pyrimidine as a pale yellow solid (11.1 g, 22.6 mmol, 96%).

MS (ESI): 491 (MH⁺).

Alternatively, the starting material was prepared as follows:

To a stirred suspension 1-(methylsulfonyl)-4-[5-(2,2,2-trifluoroethoxy)pyridin-2-yl]piperazine (23 g, 67.8 mmol, prepared as above) in THF (450 mL) at −65° C., was added drop wise a solution of LiHMDS in THF (149 mL, 1.0M solution, 149 mmol). Stirred for 30 minutes. Added diethyl chlorophosphate (11.3 mL, 78 mmol) and stirred for 1 hour. The solution was treated drop wise with a solution of 3-(2-pyridinyl)propaldehyde (12 g, 88.1 mmol) in THF (290 mL) and then allowed to warm to 0° C. over 3 hours before being quenched with a solution of hydroxylamine (41 mL, 50% aqueous solution in water, 680 mmol). The reaction was stirred for 16 hours at RT. The reaction washed with sat. NH4Cl (250 mL) back-extracting with ethyl acetate (250 mL). The combined organic extracts were then dried (brine and MgSO₄), filtered and concentrated in vacuo. The residue was then triturated with ether for 1 hour, filtered and dried to give 2-[3-(hydroxyamino)-4-({4-[5-(2,2,2-trifluoroethoxy)pyridin-2-yl]piperazin-1-yl}sulfonyl)butyl]pyrimidine (31.5 g, 64.3 mmol, 95%).

¹H NMR (CDCl₃): 8.65 (d, 2 H), 8.0 (d, 1 H), 7.25 (dd, 1 H), 7.15 (t, 1 H), 6.65 (d, 1 H), 4.3 (q, 2 H), 3.55 (m, 6 H), 3.4 (t, 4 H), 3.2 (t, 2 H), 2.9 (d, 1 H), 2.25 (m, 1 H), 2.1 (m, 1 H);

MS (ESI): 491 (MH⁺).

EXAMPLE 4

Hydroxy[(1S)-2-({4-[4-(1,1,2,2-tetrafluoroethoxy)phenyl]piperazin-1-yl}sulfonyl)-1-(tetrahydro-2H-pyran-4-yl)ethyl]formamide

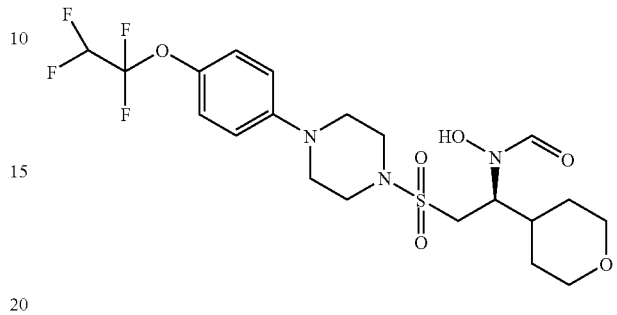

To a ice-cooled solution of 1-{[(2S)-2-(hydroxyamino)-2-(tetrahydro-2H-pyran-4-yl)ethyl]sulfonyl}-4-[4-(1,1,2,2-tetrafluoroethoxy)phenyl]piperazine (52.9 g, 0.1 mol) in a mixed solvent system of THF/formic acid (1 L/20 mL) was added a preformed mixture of formic acid (19 mL) and acetic anhydride (65 mL). The mixture was stirred at room temperature overnight. The solvents were then evaporated to low volume and the residue partitioned between dichloromethane (500 mL) and saturated sodium hydrogen carbonate solution. The organic layer was separated, dried (MgSO₄), filtered and concentrated to an oil. This was then stirred overnight in methanol (500 mL) and then concentrated to yield the monoformylated product as a white solid. The solid contained a few impurities therefore it was stirred in diethyl ether for 4 hours before being filtered and dried to yield hydroxy[(1S)-2-({4-[4-(1,1,2,2-tetrafluoroethoxy)phenyl]piperazin-1-yl}sulfonyl)-1-(tetrahydro-2H-pyran-4-yl)ethyl]formamide. (51.41 g, 92%).

Hydroxy[(1S)-2-({4-[4-(1,1,2,2-tetrafluoroethoxy)phenyl]piperazin-1-yl}sulfonyl)-1-(tetrahydro-2H-pyran-4-yl)ethyl]formamide (51.4 g) was dissolved in hot methanol (80 mL) and then allowed to cool slowly overnight to room temperature. The white crystalline solid was filtered and dried. This solid was then stirred in isopropanol (190 mL) for 24 hours before being filtered and dried at 50° C. overnight. The crystalline material washed with diethyl ether and redried for 2 days.

¹H NMR (DMSO-D₆): 9.95 and 9.60 (1 H, s), 8.30 and 8.00 (1 H, s), 7.15 (2 H, d), 7.05 (2 H, d), 6.75 (1 H, tt), 4.45 and 3.85 (1 H, t), 3.85 (2 H, m), 3.40 (2 H, m), 3.25 (10 H, m), 1.75 (2 H, m), 1.50 (1 H, m), 1.25 (2 H, m);

MS (ES) 514 (MH⁺);

Mpt 175-176° C.

The starting material was prepared as follows:

1-Bromo-4-tetrafluoroethoxybenzene (CAS Number 68835-05-9, 12 g, 0.044M) was dissolved in toluene (250 ml) under an argon atmosphere. N-Boc-piperazine (CAS Number 57260-71-6, 9.79 g, 0.053M), sodium t-butoxide (5.93 g, 0.062M), BINAP (96 mg) and dipalladium-tri-dibenzylidene acetone (96 mg) were added. Stirred at 80° C. for 4 hours, cooled and filtered off the insoluble material (washing with toluene). The filtrate was evaporated to dryness to yield crude t-butyl 4-[4-(1,1,2,2-tetrafluoroethoxy)phenyl]piperazine-1-carboxylate. Yield 15.36 g (92%).

¹H NMR (CDCL₃): δ 7.10 (D, 2H), 6.90 (D,2H), 5.90 (TT,1H), 3.60 (M,4H), 3.15 (M,4H), 1.50 (S,9H);
MS (ES): 323.0 (MH-t-BUTYL).

Crude t-butyl 4-[4-(1,1,2,2-tetrafluoroethoxy)phenyl]piperazine-1-carboxylate (15.30 g, 0.04M) was dissolved in DCM (150 ml) and TFA (30 ml) was added. The mixture was stirred at room temperature overnight, evaporated to dryness and azeotroped with toluene. The residue was partitioned between ethyl acetate and saturated sodium bicarbonate solution and the organic phase was collected, dried over MgSO₄, filtered and evaporated to dryness to yield 1-[4-(1,1,2,2-tetrafluoroethoxy)phenyl]piperazine as a solid (10.97 g, 98%)

¹H NMR (CDCl₃): δ 7.15 (d, 2H), 6.90 (d, 2H), 5.90 (t, 1H), 3.35 (m, 8H);
MS (ES): 279.0.

1-[4-(1,1,2,2-tetrafluoroethoxy)phenyl]piperazine (10.95 g, 0.04) was dissolved in DCM (500 ml) and triethylamine (18.5 ml, 0.13 mol) was added. The mixture was cooled to 0° C. and methane sulphonyl chloride (7.4 ml, 0.048 mol) added. Allowed to reach ambient temperature and stirred overnight. The reaction mixture washed with water and the organic phase collected, dried over MgS_{O4}, filtered and evaporated to dryness. The residual solid was crystallised from ethanol to yield 1-(methylsulfonyl)-4-[4-(1,1,2,2-tetrafluoroethoxy)phenyl]piperazine as a white solid. Yield 12.3 g (78.5%)

¹H NMR (CDCl₃): δ 7.15 (d, 2H), 6.95 (d, 2H), 5.9 (tt,1H), 3.35 (m,4H), 3.3 (m,4H), 2.8 (s, 3H);
MS (ES): 357.26 (MH⁺).

The 1-(methylsulfonyl)-4-[4-(1,1,2,2-tetrafluoroethoxy)phenyl]piperazine (2.85 g, 0.008 mol) was dissolved in anhydrous THF (200 ml) and cooled to −10° C. under an argon atmosphere. 1.0M solution of lithium bis(trimethylsilyl)amide in THF (17.6 ml, 0.0176 mol) was added with cooling to −30° C. and the mixture added a solution of methyl-tetrahydro-2H-pyran-4-carboxylate (CAS Number 110238-91-0) in THF (2 ml). This was allowed to reach room temperature and stirred for 2 hours. The reaction was quenched with saturated NH₄Cl solution and diluted with H₂O and ethyl acetate. The organic phase was collected, dried over MgSO₄, filtered and evaporated to dryness to yield crude 2-({4-[4-(1,1,2,2-tetrafluoroethoxy)phenyl]piperazin-1-yl}sulfonyl)-1-(tetrahydro-2H-pyran-4-yl)ethanone. (3.64 g, 97%)

¹H NMR (CDCl₃): δ 7.15 (d, 2H), 6.95 (d, 2H), 5.90 (tt, 1H), 4.05 (s, 2H), 4.00 (m, 2H) 3.50 (m, 6H), 3.25 (m, 4H), 2.95 (m, 1H), 1.85 (m, 2H), 1.70 (m, 2H);
MS (ES): 469.08 (MH⁺).

Crude 2-({4-[4-(1,1,2,2-tetrafluoroethoxy)phenyl]piperazin-1-yl}sulfonyl)-1-(tetrahydro-2H-pyran-4-yl)ethanone (3.60 g, 0.008M) was dissolved in DCM (120 ml) and methanol (40 ml) at ambient temperature and sodium borohydride (334 mg, 0.0088 mol) was added. Stirred for 2 hours, added H₂O (250 ml) and extracted with DCM. Collected the organic phase, dried over MgSO₄, filtered and evaporated to dryness to yield 2-({4-[4-(1,1,2,2-tetrafluoroethoxy)phenyl]piperazin-1-yl}sulfonyl)-1-(tetrahydro-2H-pyran-4-yl)ethanol (3.6 g, 95%).

¹H NMR (CDCl₃): δ 7.15 (d, 2H), 6.90 (d, 2 H), 5.90 (tt, 1H), 4.00 (m, 2H), 4.00 (m, 1H) 3.45 (m, 4H), 3.40 (m, 2H), 3.25 (m, 4H), 3.10 (m, 2H), 3.05 (m, 1H), 1.75 (m, 2H), 1.50 (m, 3H);
MS (ES): 471.08 (MH⁺).

2-({4-[4-(1,1,2,2-tetrafluoroethoxy)phenyl]piperazin-1-yl}sulfonyl)-1-(tetrahydro-2H-pyran-4-yl)ethanol (3.6 g, 0.008M) was dissolved in DCM (100 ml) and triethylamine (5.58 ml, 0.04 mol) was added. The mixture was cooled to 0° C. and methane sulphonyl chloride (0.94 ml, 0.012M) added with stirring at room temperature overnight. Water was added and the organic phase separated off, dried over MgS_{O4}, filtered and evaporated to dryness to yield 1-[4-(1,1,2,2-tetrafluoroethoxy)phenyl]-4-{[(E)-2-(tetrahydro-2H-pyran-4-yl)vinyl]sulfonyl}piperazine. Yield (3.15 g, 86.6%).

¹H NMR (CDCl₃): δ 7.1 (d,2H), 6.9 (d,2 H), 6.75 (dd, 1H), 6.1 (d,1H), 5.85 (tt,1H), 4.0 (m, 2H), 3.4 (m,2H), 3.25 (m,8H), 2.5 (m,1H), 1.7 (m, 2H), 1.55 (m,2H);
MS (ES): 452.88 (MH+).

1-[4-(1,1,2,2-tetrafluoroethoxy)phenyl]-4-{[(E)-2-(tetrahydro-2H-pyran-4-yl)vinyl]sulfonyl}piperazine (3.13 g, 0.007 mol) was dissolved in THF (50 ml) and 50% hydroxylamine in H₂O (12 ml) was added. Stirred at ambient temperature overnight, quenched with saturated NH₄Cl solution and extracted with ethyl acetate. The organic phase was dried over MgSO4, filtered and evaporated to dryness to yield racemic 1-{[2-(hydroxyamino)-2-(tetrahydro-2H-pyran-4-yl)ethyl]sulfonyl}-4-[4-(1,1,2,2-tetrafluoroethoxy)phenyl]piperazine This was separated into its enantiomers using an AD Chiralpak chiral prep HPLC column and eluting with 20% methanol/acetonitrile. The second compound off the column gave the required enantiomer, 1-{[(2S)-2-(hydroxyamino)-2-(tetrahydro-2H-pyran-4-yl)ethyl]sulfonyl}-4-[4-(1,1,2,2-tetrafluoroethoxy)phenyl]piperazine.

¹H NMR (CDCl₃): δ 7.2 (d, 2H), 6.9 (d, 2H), 5.9 (tt, 1H), 3.85 (m, 2H), 3.5-3.1 (m, 11H), 3.05 (m, 2H), 1.951.8 (dd, 2H), 1.6 (d, 2H), 1.35 (m, 2H);
MS (ES): 485.92 (MH+).

EXAMPLE 5

Hydroxy[1-phenyl-2-({4-[4-(1,1,2,2-tetrafluoroethoxy)phenyl]piperazin-1-yl}sulfonyl)ethyl]formamide

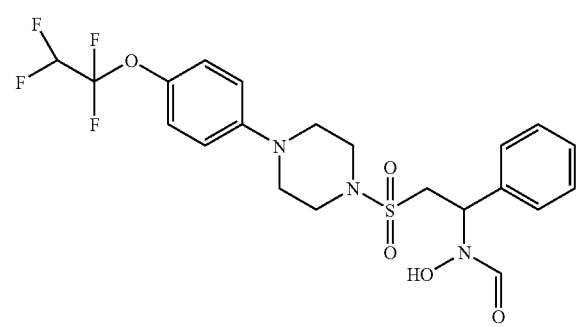

This compound was prepared using the method given in Example 4

¹H NMR (CDCl₃): 8.45 and 8.2 (d, 1H), 7.4 (m, 5H), 7.15 (d, 2H), 6.85 (d, 2H), 5.9 (tt, 1H), 5.5 (d, 1H), 3.4 (br s, 4H), 3.3 (s2H), 3.15 (br, 4H).

The intermediate 1-[(-2-phenylvinyl)sulphonyl]-4-[4-(1,1,2,2-tetrafluoroethoxy)phenyl]piperazine was prepared as shown below:

1-[4-(1,1,2,2-tetrafluoroethoxy)phenyl]piperazine (1.39 g, 0.005 mol) was dissolved in DCM (250 ml) and triethylamine (2.1 ml, 0.015 mol) was added. This was cooled to 0° C. and styrene sulphonyl chloride (CAS Number 52147-97-4, 1.11 g, 0.0055 mol) was added. Allowed to reach ambient temperature and stirred overnight. Washed with H₂O and separated off the organic phase. Dried over MgSO₄, filtered and evaporated to dryness to an oil which was purified by flash column chromatography (Merck 9385 silica), eluting with 80% iso-hexane/ethyl acetate to yield 1-[(-2-phenylvinyl)sulphonyl]-4-[4-(1,1,2,2-tetrafluoroethoxy)phenyl]piperazine as a yellow solid. Yield 650 mg (25%)

¹H NMR (CDCl₃): δ 7.5 (m,3H), 7.4 (m,3H), 7.15 (d,2H), 6.9 (d,2H), 6.7 (d,1H), 5.85 (tt,1H), 3.4 (m,4H), 3.25 (m,4H);

MS (ES): 445.27 (MH+).

EXAMPLE 6

Hydroxy{4-pyrimidin-2-yl-1-[({4-[4-(1,1,2,2-tetrafluoroethoxy)phenyl]piperazin-1-yl}sulfonyl)methyl]butyl}formamide

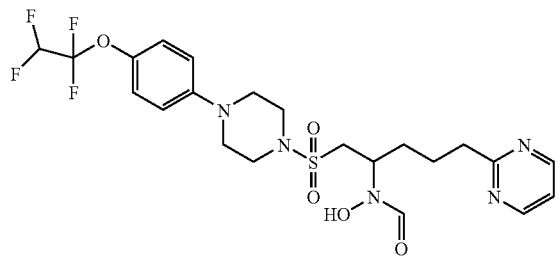

This compound was prepared using the method given in Example 4

MS (ES): 550.03 (MH⁺).

The intermediate 2-[5-({4-[4-(1,1,2,2-tetrafloroethoxy)phenyl]piperazin-1-yl}sulphonyl)pent-4-en-1-yl]pyrimidine was prepared as shown below:

1-(methylsulfonyl)-4-[4-(1,1,2,2-tetrafluoroethoxy)phenyl]piperazine (356 mg, 0.001 mol) was dissolved in anhydrous THF (100 ml) and cooled to −10° C. under an argon atmosphere. 1.0 mol solution of lithium bis-(trimethylsilyl)amide in THF (2.2 ml, 0.0022 mol) was added and stirred at −10° C. for 30 minutes, followed by addition of diethylchlorophosphate (0.15 ml, 0.001 mol) with stirring at −10° C. for a further 30 minutes. A solution of 2-pyrimidinyl-4-butyraldehyde in anhydrous THF (5 ml) was added, the mixture stirred at −10° C. for 60 minutes and while still cold the reaction was quenched with saturated NH₄Cl solution. Following dilution with H₂O and ethyl acetate, the organic phase was collected, dried over MgSO₄, filtered and evaporated to dryness to yield an oil. Purification by flash column chromatography (Merck9385 silica), eluting with ethyl acetate gave 2-[5-({4-[4-(1,1,2,2-tetrafloroethoxy)phenyl]piperazin-1-yl}sulphonyl)pent-4-en-1-yl]pyrimidine. Yield 230 mg (47%).

¹H NMR (CDCl₃): 8.8 (d,2H), 7.2 (s,1H), 7.1 (d,2H), 6.85 (d,2H), 6.2 (d,2H), 5.8 (tt,1H), 4.05 (br,1H), 3.25 (br,8H), 3.05 (m,2H), 2.3 (m,1H), 2.05 (m,2H), 1.4 (m, 2H);

MS (ESI): 489 (MH+).

EXAMPLE 7

The following compounds were also synthesised

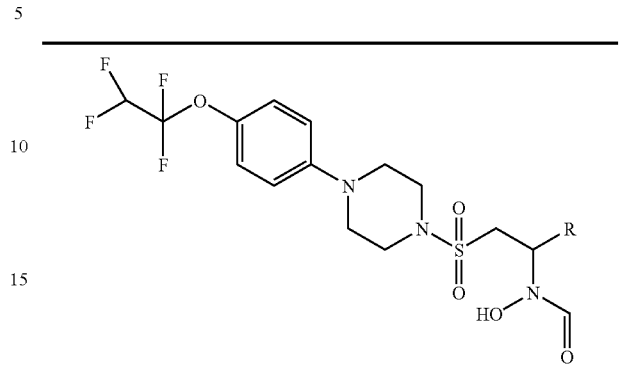

| No. | R | Racemate or S enantiomer | MH+ | Prepared using method in example |
|---|---|---|---|---|
| a | 2-PyrimidinylCH2CH2CH2 | S enantiomer | 550.00 | 6 I |
| b | 5-F-2-PyrimidinylCH2CH2 | Racemate | 554.17 | 6 |
| c | 5-F-2-PyrimidinylCH2CH2 | S enantiomer | 553.94 | 6 II |
| d | 2-PyrimidinylCH2CH2 | Racemate | 535.98 | 6 |
| e | 2-PyrimidinylCH2CH2 | S enantiomer | 535.98 | 6 II |
| f | ethyl | Racemate | 457.95 | 6 |
| g | methyl | Racemate | 443.97 | 6 |

I enantiomer separated by an OJ chiral prep HPLC column, eluting with methanol
II enantiomer separated by an AD chiralpak prep HPLC column, eluting with 20% methanol/acetonitrile

EXAMPLE 8

The following compounds were prepared as described in previous examples.

| No. | R | | MH+ | Prepared using method in example |
|---|---|---|---|---|
| a | Racemate | 2-PyrimidinylCH2CH2 | 517.99 | 6 |
| b | S enantiomer | 2-PyrimidinylCH2CH2 | 518.12 | 6 I |
| c | Racemate | 5-F-2-PyrimidinylCH2CH2 | 535.88 | 6 |
| d | S enantiomer | 5-F-2-PyrimidinylCH2CH2 | 536.00 | 6 II |
| e | Racemate | 2-PyrimidinylCH2CH2CH2 | 531.88 | 6 |
| f | S enantiomer | 2-PyrimidinylCH2CH2CH2 | 532.04 | 6 I |
| g | S enantiomer | 4-tetrahydropyran | 496.10 | 4 III |

I Separated on a Chiralpak AD column, eluting with 10% MeOH, MeCN
II Separated on a Chiralpak AD column, eluting with 15% MeOH, MeCN
III Separated at the hydroxylamine stage on a a Chiralpak AD column, eluting with 20% MeOH, MeCN The starting material for these syntheses was prepared as follows:

1-(methylsulfonyl)-4-[4-(2,2,2-trifluoroethoxy)phenyl]piperazine

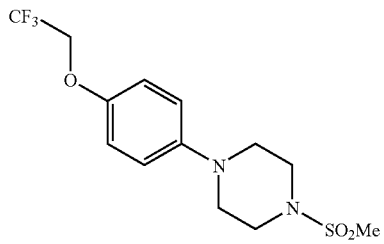

Potassium carbonate (22.89 g, 166 mmol) and 2,2,2-trifluoroethyl trifluoromethanesulfonate (16.0 g, 69 mmol) were added to a solution of 4-bromophenol (9.57 g, 55 mmol) in acetone (200 mL). The reaction was stirred at room temperature overnight then filtered and concentrated at 300 mbar, 30° C. to remove the acetone. This yielded 1-bromo-4-(2,2,2-trifluoroethoxy)benzene as a waxy solid (>100% yield as some acetone still present).

$^1$H NMR (DMSO-D$_6$), δ: 7.50 (2 H, d), 7.05 (2 H, d), 4.75 (2 H, q).

1-bromo-4-(2,2,2-trifluoroethoxy)benzene (14.5 g, 57 mmol) was dissolved in toluene (250 ml) under an argon atmosphere. tert-Butyl piperazine-1-carboxylate (12.7 g, 68 mmol), sodium tert-butoxide (7.6 g, 79.5 mmol) rac-2,2'-bis(diphenylphosphino)-1,1'-binaphthyl (200 mg, 0.32 mmol) and tris(dibenzylideneacetone)dipalladium(0) (200 mg, 0.2 mmol) were added and the reaction heated to 80° C. for 4 hours. The mixture was then cooled and filtered through Celite to yield crude tert-butyl 4-[4-(2,2,2-trifluoroethoxy)phenyl]piperazine-1-carboxylate (32.47 g).

$^1$H NMR (400 MHz, CDCl$_3$): δ 6.90 (4 H, s), 4.30 (2 H, q), 3.60 (4 H, m), 3.05 (4 H, m), 1.45 (9 H, s);

m/z (ES) 305 (MH$^+$-$^t$Bu).

Crude tert-butyl 4-[4-(2,2,2-trifluoroethoxy)phenyl]piperazine-1-carboxylate (32.47 g, approx 57 mmol) was dissolved in DCM (300 ml) and TFA (69 mL) was added. The reaction was stirred at room temperature overnight then evaporated to dryness, azeotroping with toluene. The residue was partitioned between DCM and saturated sodium bicarbonate solution. The organic phase was separated, dried (MgSO$_4$), filtered and concentrated to yield 1-[4-(2,2,2-trifluoroethoxy)phenyl]piperazine as a solid (13.48 g, 91%)

$^1$H NMR (400 MHz, CDCl$_3$): δ 6.90 (4 H, s), 4.30 (2 H, q), 3.30 (8 H, m);

MS (ES) 261 MH$^+$.

1-[4-(2,2,2-trifluoroethoxy)phenyl]piperazine (13.48 g, 50 mmol) was dissolved in DCM (500 mL) and cooled to 0° C. Triethylamine (29 mL, 0.2 mol) was added, followed by the dropwise addition of methanesulfonyl chloride (4.2 mL, 55 mmol). The reaction was then allowed to warm to room temperature and stir overnight, before being quenched by the addition of water. The layers were separated, and the organic phase dried (MgSO$_4$), filtered and concentrated. The residue was recrystallised from hot ethanol to give pure 1-(methylsulfonyl)-4-[4-(2,2,2-trifluoroethoxy)phenyl]piperazine (3.3 g, 18%).

$^1$H NMR (CDCl$_3$): δ 6.90 (4 H, s), 4.30 (2 H, q), 3.40 (4 H, m), 3.20 (4 H, m), 2.85 (3 H, s);

m/z (ES) 339 MH$^+$.

The invention claimed is:

1. A compound of formula (I)

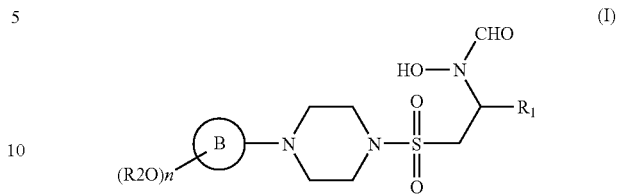

or a pharmaceutically acceptable salt thereof,
wherein ring B represents a monocyclic aryl ring having six ring atoms or a monocyclic heteroaryl ring having up to six ring atoms and containing one or more ring heteroatoms wherein each said heteroatom is nitrogen;

R2 represents a group selected from C1-6 alkyl or aryl, which said group is substituted by one or more fluorine groups;

n is 1, 2 or 3; and

R$_1$ represents an optionally substituted group selected from C1-6 alkyl, C5-7 cycloalkyl, heterocycloalkyl, aryl, heteroaryl, C1-6 alkyl-aryl, C1-6alkyl-heteroaryl, C1-6 alkyl-cycloalkyl or C1-6alkyl-heterocycloalkyl.

2. A compound according to claim 1 wherein B is monocyclic aryl ring having six ring atoms or a monocyclic heteroaryl ring having up to six ring atoms and containing from one to four nitrogen ring atoms.

3. A compound according to claim 1 wherein ring B is phenyl, pyridinyl or pyrimidinyl.

4. A compound according to claim 1 wherein R2 is a C1-6 alkyl group substituted by one to five fluorine groups.

5. A compound according to claim 1 wherein R2 is substituted by three or four fluorine groups.

6. A compound according to claim 5 wherein R2 is the group —CF2CHCF2.

7. A compound according to claim 5 wherein R2 is the group —CH2CF3.

8. A compound according to claim 1 wherein n is 1.

9. A compound according to claim 1 wherein R$_1$ is an optionally substituted group selected from C1-4 alkyl, aryl having six ring atoms, a five to six membered heterocycloalkyl ring comprising one or two ring heteroatoms, which may be the same or different, selected from N, O and S or a C1-4 alkyl-heteroaryl group wherein the heteroaryl has up to six ring atoms and comprises one or two ring heteroatoms selected from N, O and S.

10. A compound according to claim 9 wherein R$_1$ is an optionally substituted five to six membered heterocycloalkyl ring comprising one or two ring heteroatoms, which may be the same or different, selected from N, O and S, or a C1-4alkyl-heteroaryl group having up to six ring atoms and comprising one or more heteroatoms, which may be the same or different, selected from N, O and S, optionally substituted on the heteroaryl ring.

11. A compound according to claim 9 wherein R$_1$ is unsubstituted.

12. A compound according to claim 9 wherein R$_1$ is substituted by one or two substituents, which may be the same or different, selected from C1-4 alkyl, halogen, CF3 and CN.

13. A compound according to claim 12 wherein R$_1$ is substituted by fluorine.

14. A compound according to claim 11 wherein $R_1$ is tetrahydropyranyl, 2-pyrimidinyl-CH2CH2-, 2-pyrimidinyl-CH2CH2CH2- or 5-F-2-pyrimidinyl-CH2CH2-.

15. A compound according to claim 1 wherein R2 is C1-6 alkyl, substituted by one to five fluorine groups; n is 1; ring B is phenyl, pyridinyl or pyrimidinyl and $R_1$ is an optionally substituted five to six membered heterocycloalkyl ring comprising one or two ring heteroatoms, which may be the same or different, selected from N, O and S, or a C1-4alkyl-heteroaryl group having up to six ring atoms and comprising one or more heteroatoms, which may be the same or different, selected from N, O and S, optionally substituted on the heteroaryl ring.

16. A pharmaceutical composition comprising a compound of formula (I), or a pharmaceutically acceptable salt thereof, as claimed in claim 1 in association with a pharmaceutically acceptable adjuvant, diluent or carrier.

17. A process for the preparation of a pharmaceutical composition as claimed in claim 16 which comprises mixing a compound of formula (I), or a pharmaceutically acceptable salt thereof, as defined in claim 1 with a pharmaceutically acceptable adjuvant, diluent or carrier.

18. A process for the preparation of a compound of formula (I) as claimed in claim 1, or a pharmaceutically acceptable salt thereof, which comprises:

converting the appropriate hydroxyamino compound of the formula (IV),

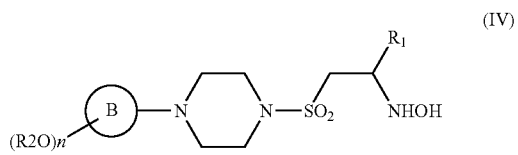

wherein R2, n, ring B and $R_1$ are as defined in formula (I),
into a compound of formula (I) by formylation with a mixed anhydride;
and optionally thereafter carrying out one or more of the following:
converting the compound obtained into a further compound of formula (I) as claimed in claim 1 and/or forming a pharmaceutically acceptable salt of the compound.

19. A compound of formula (III)

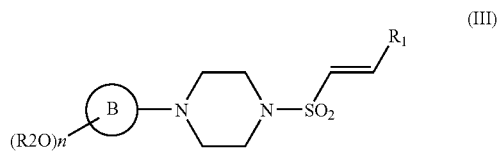

wherein ring B represents a monocyclic aryl ring having six ring atoms or a monocyclic heteroaryl ring having up to six ring atoms and containing one or more ring heteroatoms wherein each said heteroatom is nitrogen;
R2 represents a group selected from C1-6 alkyl or aryl, which said group is substituted by one or more fluorine groups;
n is 1, 2 or 3; and
$R_1$ represents an optionally substituted group selected from C1-6 alkyl, C5-7 cycloalkyl, heterocycloalkyl, aryl, heteroaryl, C1-6 alkyl-aryl, C1-6alkyl-heteroaryl, C1-6 alkyl-cycloalkyl or C1-6alkyl-heterocycloalkyl.

20. A compound of formula (IV)

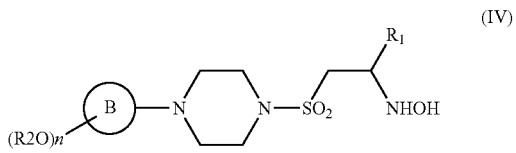

wherein ring B represents a monocyclic aryl ring having six ring atoms or a monocyclic heteroaryl ring having up to six ring atoms and containing one or more ring heteroatoms wherein each said heteroatom is nitrogen;
R2 represents a group selected from C1-6 alkyl or aryl, which said group is substituted by one or more fluorine groups;
n is 1, 2 or 3; and
$R_1$ represents an optionally substituted group selected from C1-6 alkyl, C5-7 cycloalkyl, heterocycloalkyl, aryl, heteroaryl, C1-6 alkyl-aryl, C1-6alkyl-heteroaryl, C1-6 alkyl-cycloalkyl or C1-6alkyl-heterocycloalkyl.

21. The process of claim 18, wherein the mixed anhydride is prepared from reaction of formic acid and acetic anhydride.

* * * * *